United States Patent
Shibuya et al.

(10) Patent No.: US 10,459,002 B2
(45) Date of Patent: Oct. 29, 2019

(54) MOTION ANALYSIS METHOD AND MOTION ANALYSIS DEVICE

(71) Applicant: SEIKO EPSON CORPORATION, Tokyo (JP)

(72) Inventors: Kazuhiro Shibuya, Shiojiri (JP); Kazuo Nomura, Shiojiri (JP); Kenya Kodaira, Azumino (JP); Masafumi Sato, Hara-mura (JP)

(73) Assignee: SEIKO EPSON CORPORATION, Tokyo (JP)

( * ) Notice: Subject to any disclaimer, the term of this patent is extended or adjusted under 35 U.S.C. 154(b) by 1058 days.

(21) Appl. No.: 14/306,684

(22) Filed: Jun. 17, 2014

(65) Prior Publication Data

US 2014/0379294 A1     Dec. 25, 2014

(30) Foreign Application Priority Data

Jun. 21, 2013 (JP) ................................. 2013-130654

(51) Int. Cl.
*G01P 13/02* (2006.01)
*A61B 5/11* (2006.01)
(Continued)

(52) U.S. Cl.
CPC ............ *G01P 13/02* (2013.01); *A61B 5/1121* (2013.01); *A61B 5/1122* (2013.01);
(Continued)

(58) Field of Classification Search
CPC .......... G01P 13/00; G01P 7/00; A61B 5/1121; A61B 5/1122; A61B 5/6895; A61B 5/743; A61B 2562/0219; G06K 9/00342
(Continued)

(56) References Cited

U.S. PATENT DOCUMENTS

2006/0111197 A1    5/2006  Yamamoto et al.
2009/0247312 A1*  10/2009  Sato ................... A63B 69/3632
                                                        473/223
(Continued)

FOREIGN PATENT DOCUMENTS

JP    A-11-169499    6/1999
JP    A-2004-24488   1/2004
(Continued)

OTHER PUBLICATIONS

Grober, Measuring Tempo, Rhythm, Timing and the Torques that Generate Power in the Golf Swing, Jan. 2010 (Year: 2010).*
(Continued)

*Primary Examiner* — Michael P Nghiem
*Assistant Examiner* — Dacthang P Ngo
(74) *Attorney, Agent, or Firm* — Oliff PLC

(57) ABSTRACT

A motion analysis method includes calculating a change in an amount of inertia of a region attached with an inertial sensor during a swing using an output of the inertial sensor, and identifying a maximum value of the amount of inertia during the swing to compare the maximum value and the amount of inertia at an impact with each other. A deceleration timing during the swing of the region (the grip of the sporting equipment) attached with the inertial sensor is identified, and the quality of the swing can be evaluated.

12 Claims, 5 Drawing Sheets

(51) Int. Cl.
*A61B 5/00* (2006.01)
*G01P 7/00* (2006.01)
*G06K 9/00* (2006.01)

(52) U.S. Cl.
CPC ............ *A61B 5/6895* (2013.01); *A61B 5/743* (2013.01); *G01P 7/00* (2013.01); *G06K 9/00342* (2013.01); *A61B 2562/0219* (2013.01)

(58) Field of Classification Search
USPC ........................................................ 702/141
See application file for complete search history.

(56) References Cited

U.S. PATENT DOCUMENTS

| | | | |
|---|---|---|---|
| 2012/0157241 A1* | 6/2012 | Nomura | A63B 69/0002 473/422 |
| 2014/0200094 A1* | 7/2014 | Parke | A63F 13/00 473/223 |

FOREIGN PATENT DOCUMENTS

| | | |
|---|---|---|
| JP | 2006-109988 A | 4/2006 |
| JP | 2006-141984 A | 6/2006 |
| JP | 2007-325713 A | 12/2007 |
| JP | A-2008-73210 | 4/2008 |
| JP | A-2009-125507 | 6/2009 |
| JP | A-2010-11926 | 1/2010 |
| JP | 2013-99527 A | 5/2013 |

OTHER PUBLICATIONS

Kinematic Sequence: Transition and Downswing Phases, Feb. 2008 (Year: 2008).*

ACCESS initiates "Fullmiere Cloud", cloud service for 3D golf swing analyzing product; Apr. 15, 2013.

Horiuchi, Shoichi. et al. "Regarding Movement Training Using Video Comparison System". 14pgs, Dec. 26, 2017.

Octal Co. JP, and Kanda, Hiroyuki. "Concerning Guidance for Motion Using Image Comparing System," Japan Society of Coaching Studies (JSCS), the 22nd Meeting, Apr. 12, 2011.

* cited by examiner

MOTION ANALYSIS METHOD AND MOTION ANALYSIS DEVICE

BACKGROUND

1. Technical Field

The present invention relates to a motion analysis method and a motion analysis device.

2. Related Art

A motion analysis device is used for an analysis of a motion such as a swing action. When the sporting equipment is swung at the swing action, the posture of the sporting equipment varies in accordance with the time axis. An inertial sensor is mounted on the sporting equipment or a hand of the subject. The swing action is visually reproduced based on an output of the inertial sensor. As a specific example of such a motion analysis device, there can be cited, for example, a golf swing analysis device as disclosed in JP-A-2008-73210.

For example, a golf swing starts with address, and then reaches follow-through and then finish via swinging up in a backswing, a downswing after a lag, and an impact. It has been known that if the speed of the grip is decelerated before the impact, the head speed of the golf club at the impact can be increased. However, currently, it has not been realized to measure the deceleration of the grip with a motion analysis device and to coach a golfer while indicating the result.

SUMMARY

An advantage of at least one of the aspects of the invention is to provide a motion analysis method and a motion analysis device adapted to calculate the deceleration of the grip of the sporting equipment as one of the indexes in the motion analysis.

(1) A motion analysis method according to an aspect of the invention includes calculating a change in an amount of inertia of a region attached with an inertial sensor during a swing using an output of the inertial sensor, and identifying a maximum value of the amount of inertia during the swing to compare the maximum value and the amount of inertia at an impact.

When the sporting equipment is swung at the swing action, the posture of the sporting equipment varies in accordance with the time axis. It has been known that if the speed of the grip is decelerated before the impact, the head speed of the sporting equipment at the impact can be increased. The inertial sensor outputs a detection signal in accordance with the change in the position and the posture of the region (e.g., the sporting equipment or the hand of the subject) to which the inertial sensor is attached, and the amount of inertia is calculated from the detection signal thus output. The maximum value of the amount of inertia of the region attached with the inertial sensor is identified based on the change in the amount of inertia thus calculated. The maximum value in the region attached with the sensor identified in such a manner is compared with the amount of inertia at impact, and is presented to the subject. By comparing the maximum value and the amount of inertia at impact, the deceleration timing of the swing and whether or not an appropriate deceleration is performed can be checked. The subject can improve the form of the swing in accordance with the deceleration timing of the swing thus presented.

(2) The motion analysis method of the aspect of the invention may include calculating a ratio between the maximum value of the amount of inertia during the swing and the amount of inertia at the impact. The ratio of the deceleration of the swing can quantitatively be presented to the subject.

(3) A motion analysis method according to another aspect of the invention includes calculating a change in an amount of inertia of a region attached with an inertial sensor during a swing using an output of the inertial sensor, and detecting a timing when the amount of inertia turns from increase to decrease during the swing. The timing when the amount of inertia turns from increase to decrease in the swing can be identified as the deceleration timing. The subject can improve the form of the swing in accordance with the deceleration timing of the swing thus presented.

(4) In the motion analysis method of the aspect of the invention, the amount of inertia may be a moving speed. By using the moving speed as the amount of inertia, the amount of inertia can be shown as a common parameter for the subject, and the subject can improve the form of the swing without confusion.

(5) In the motion analysis method of the aspect of the invention, the inertial sensor may be attached to at least one of sporting equipment used for the swing, and a hand of a subject. It is preferable that the inertial sensor is attached to a place, to which the subject can easily attach the inertial sensor, such as the shaft portion including the grip of the sporting equipment or a hand of the subject, and then the change in the amount of inertia at the position to which the sensor is attached is calculated.

(6) In the motion analysis method of the aspect of the invention, the change in the amount of inertia during the swing may be displayed in a time-series manner. By displaying the change in the amount of inertia, the subject can improve the form of the swing while watching the screen.

(7) In the motion analysis method of the aspect of the invention, the amount of inertia of a region attached with the inertial sensor and the amount of inertia of a hitting region of sporting equipment used for the swing may be displayed. For example, in the case of the golf swing, by displaying the moving speed of the club head for hitting the ball and the moving speed of the grip portion attached with the inertial sensor on the same screen, the subject can check the timing of weakening the force during the swing, and the increase in moving speed of the club head after that timing.

(8) In the motion analysis method of the aspect of the invention, the timing when the amount of inertia turns from increase to decrease may be displayed together with a motion trajectory of the swing. In such a manner as described above, the deceleration of the grip is visually presented to the subject. The subject can clearly figure out the position of the deceleration of the grip during the swing action. The subject can improve the form of the swing in accordance with the moment of the deceleration of the grip presented in such a manner.

(9) A motion analysis device according to still another aspect of the invention includes a calculation section adapted to calculate the change in an amount of inertia of a region attached with an inertial sensor during a swing using an output of the inertial sensor, identify a maximum value of the amount of inertia during the swing, and compare the maximum value and an amount of inertia at an impact. By comparing the maximum value and the amount of inertia at impact, the deceleration timing of the swing and whether or not an appropriate deceleration is performed can be checked. The subject can improve the form of the swing in accordance with the deceleration timing of the swing thus presented.

BRIEF DESCRIPTION OF THE DRAWINGS

The invention will be described with reference to the accompanying drawings, wherein like numbers reference like elements.

DESCRIPTION OF AN EXEMPLARY EMBODIMENT

Hereinafter, an embodiment of the invention will be explained with reference to the accompanying drawings. It should be noted that the embodiment explained below does not unreasonably limit the content of the invention as set forth in the appended claims, and all of the constituents set forth in the embodiment are not necessarily essential as means for solving the problem according to the invention.

(1) Configuration of Golf Swing Analysis Device

Figure 1:
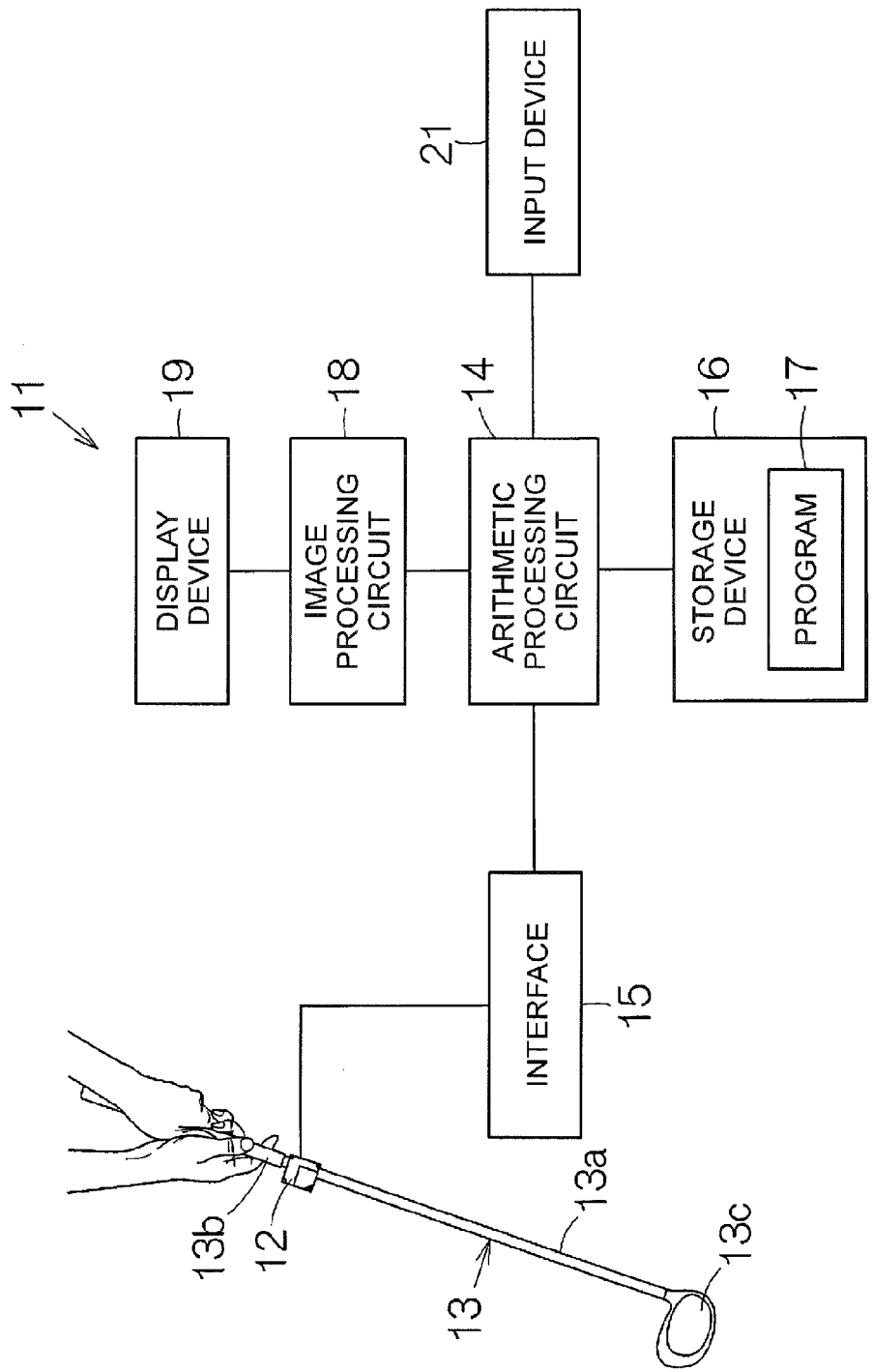
FIG. 1 is a conceptual diagram schematically showing a configuration of a golf swing analysis device according to an embodiment of the invention.

FIG. 1 schematically shows a configuration of a golf swing analysis device (a motion analysis device) 11 according to an embodiment of the invention. The golf swing analysis device 11 is provided with, for example, an inertial sensor 12. The inertial sensor 12 incorporates, for example, an acceleration sensor and a gyro sensor. The acceleration sensor is capable of separately detecting accelerations in three-axis directions perpendicular to each other. The gyro sensor is capable of individually detecting angular velocities around the three axes perpendicular to each other. The inertial sensor 12 outputs a detection signal. The detection signal identifies the acceleration and the angular velocity for each of the axes. The acceleration sensor and the gyro sensor detect the information of the accelerations and the angular velocities with relative accuracy. The inertial sensor 12 is attached to a golf club (sporting equipment) 13. The golf club 13 is provided with a shaft 13a and a grip 13b. The grip 13b is held by hand. The grip 13b is formed coaxially with the axis of the shaft 13a. A club head 13c is connected to the tip of the shaft 13a. It is desirable that the inertial sensor 12 is attached to the shaft 13a or the grip 13b of the golf club 13. It is sufficient for the inertial sensor 12 to be fixed to the golf club 13 so as to be unable to move relatively to the golf club 13. Here, when attaching the inertial sensor 12, one of the detection axes of the inertial sensor 12 is adjusted to the axis of the shaft 13a.

The golf swing analysis device 11 is provided with an arithmetic processing circuit 14. The inertial sensor 12 is connected to the arithmetic processing circuit 14. In the connection, a predetermined interface circuit 15 is connected to the arithmetic processing circuit 14. The interface circuit 15 can be connected to the inertial sensor 12 with wire, or can also be connected wirelessly to the inertial sensor 12. The arithmetic processing circuit 14 is supplied with the detection signal from the inertial sensor 12.

A storage device 16 is connected to the arithmetic processing circuit 14. The storage device 16 can store, for example, a golf swing analysis software program (a motion analysis program) 17 and related data. The arithmetic processing circuit 14 executes the golf swing analysis software program 17 to realize a golf swing analysis method. The storage device 16 can include a dynamic random access memory (DRAM), a mass-storage unit, a nonvolatile memory, and so on. For example, the DRAM temporarily holds the golf swing analysis software program 17 when performing the golf swing analysis method. The mass-storage unit such as a hard disk drive (HDD) stores the golf swing analysis software program 17 and the data. The nonvolatile memory stores a program and data relatively small in volume such as a basic input and output system (BIOS).

An image processing circuit 18 is connected to the arithmetic processing circuit 14. The arithmetic processing circuit 14 transmits predetermined image data to the image processing circuit 18. A display device 19 is connected to the image processing circuit 18. In the connection, a predetermined interface circuit (not shown) is connected to the image processing circuit 18. The image processing circuit 18 transmits an image signal to the display device 19 in accordance with the image data input. An image identified by the image signal is displayed on a screen of the display device 19. A flat panel display such as a liquid crystal display is used as the display device 19. Here, the arithmetic processing circuit 14, the storage device 16, and the image processing circuit 18 are provided as a computer system.

An input device 21 is connected to the arithmetic processing circuit 14. The input device 21 is provided with at least alphabet keys and a numerical keypad. Character information and numerical information are input to the arithmetic processing circuit 14 from the input device 21. The input device 21 can be formed of, for example, a keyboard. The combination of the computer device and the keyboard can be replaced with, for example, a smart phone, a cellular phone unit, or a tablet personal computer (PC).

(2) Motion Analysis Model

Figure 2:
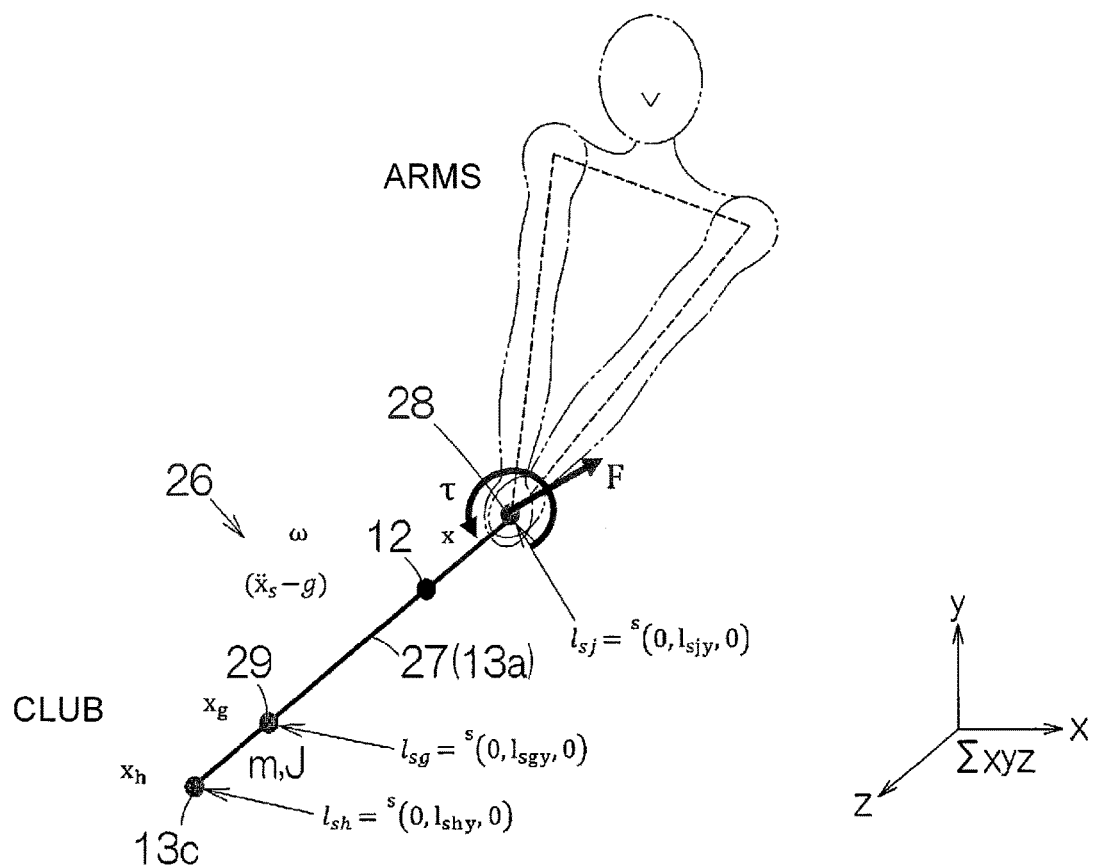
FIG. 2 is a conceptual diagram schematically showing a relationship between a motion analysis model, and a golfer and a golf club.

The arithmetic processing circuit 14 defines a virtual space. The virtual space is formed of a three-dimensional space. The three-dimensional space identifies a real space. As shown in FIG. 2, the three-dimensional space has an absolute reference coordinate system (a global coordinate system) $\Sigma_{xyz}$. In the three-dimensional space, there is built a three-dimensional motion analysis model 26 in accordance with the absolute reference coordinate system $\Sigma_{xyz}$. Point constraint by a pivot point 28 (coordinate x) is applied to a rod 27 of the three-dimensional motion analysis model 26. The rod 27 three-dimensionally acts as a pendulum around the pivot point 28. The position of the pivot point 28 can be moved. Here, in accordance with the absolute reference coordinate system $\Sigma_{xyz}$, the position of the centroid 29 of the rod 27 is identified by the coordinate $x_g$, and the position of the club head 13c is identified by the coordinate $x_h$.

The three-dimensional motion analysis model 26 corresponds to what is obtained by modeling the golf club 13 at swing. The rod 27 of the pendulum projects the shaft 13a of the golf club 13. The pivot point 28 of the rod 27 projects the grip 13b. The inertial sensor 12 is fixed to the rod 27. In accordance with the absolute reference coordinate system $\Sigma_{xyz}$, the position of the inertial sensor 12 is identified by the coordinate $x_s$. The inertial sensor 12 outputs an acceleration signal and an angular velocity signal. In the acceleration signal, an acceleration after deduction of the influence of the gravitational acceleration g is identified as $(\ddot{X}_s - g)$. Further, in the angular velocity signal, angular velocities $\omega_1, \omega_2$ are identified.

Similarly, the arithmetic processing circuit 14 fixes a local coordinate system $\Sigma_s$ to the inertial sensor 12. The origin of the local coordinate system $\Sigma_s$ is set to the origin of the detection axis of the inertial sensor 12. The y axis of the local coordinate system $\Sigma_s$ coincides with the center of the shaft 13a. The x axis of the local coordinate system $\Sigma_s$ coincides with the target direction identified by the orientation of the face. Therefore, in accordance with the local coordinate system $\Sigma_s$, the position $1_{sj}$ of the pivot point is identified by $(0, 1_{sjy}, 0)$. Similarly, on the local coordinate system $\Sigma_s$, the position $1_{sg}$ of the centroid 29 is identified by $(0, 1_{sgy}, 0)$, and the position $1_{sh}$, of the club head 13c is identified by $(0, 1_{shy}, 0)$.

(3) Configuration of Arithmetic Processing Circuit

Figure 3:
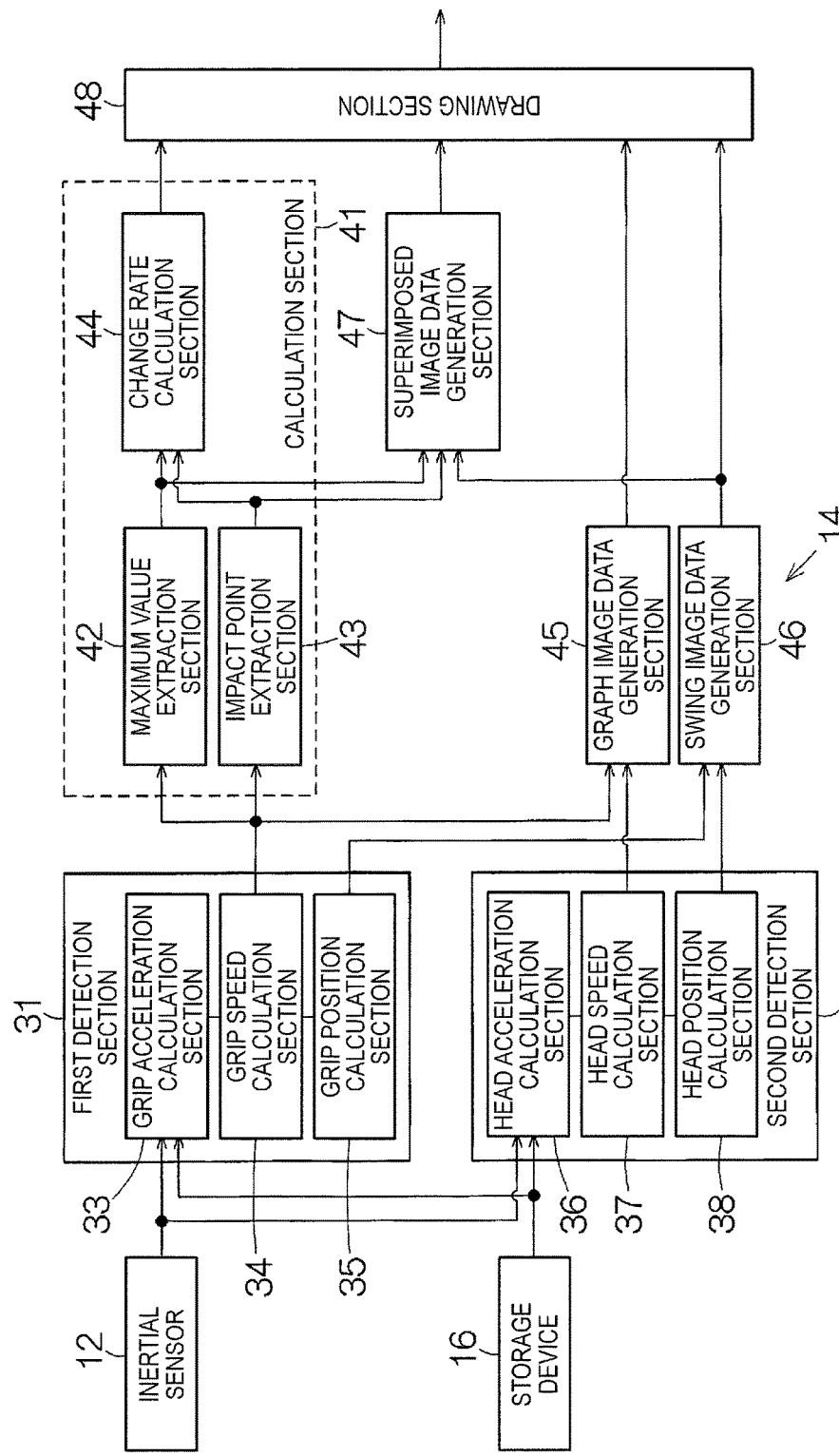
FIG. 3 is a block diagram schematically showing a configuration of an arithmetic processing circuit according to an embodiment of the invention.

FIG. 3 schematically shows a configuration of the arithmetic processing circuit 14 according to the embodiment. The arithmetic processing circuit 14 is provided with a first detection section (a detection section) 31 and a second detection section 32. The first detection section 31 and the second detection section 32 are each connected to the inertial sensor 12. The first detection section 31 and the second detection section 32 are each supplied with an output from the inertial sensor 12. The first detection section detects an amount of inertia of the grip 13b in motion based on the output of the inertial sensor 12. Similarly, the second detection section 32 detects an amount of inertia of the club head 13c in motion based on the output of the inertial sensor 12.

Here, the first detection section 31 is provided with a grip acceleration calculation section 33, a grip speed calculation section 34, and a grip position calculation section 35. The grip acceleration calculation section 33 is connected to the inertial sensor 12. The grip acceleration calculation section 33 calculates the acceleration of the grip 13b based on the output of the inertial sensor 12 in accordance with the following formula. In such a calculation of the acceleration as described above, the grip acceleration calculation section 33 identifies the position $1_{sj}$ of the grip 13b in accordance with the local coordinate system $\Sigma_s$ unique to the inertial sensor 12. When identifying the position, the grip acceleration calculation section 33 obtains the position information from the storage device 16. The storage device 16 stores the position $1_{sj}$ of the grip 13b in advance. The position $1_{sj}$ of the grip 13b can be designated via, for example, the input device 21.)

$$a_{sj} = a_s + \dot{\omega}_s \times l_{sj} + \omega_s \times (\omega_s \times l_{sj}) + g$$

The grip speed calculation section 34 is connected to the grip acceleration calculation section 33. The grip speed calculation section 34 calculates the moving speed of the grip 13b based on the output of the grip acceleration calculation section 33. When calculating the moving speed, the grip speed calculation section 34 performs an integral treatment on the acceleration having been calculated by the grip acceleration calculation section 33 in accordance with the following formula at predetermined sampling intervals dt. Here, N represents the number of samples (the same shall apply hereinafter).

$$V_{sj}(0) = 0$$

$$V_{sj}(t) = \sum_{n=1}^{t} \alpha_{sj}(n) \cdot dt \ (t = 1, \ldots, N)$$

The grip speed calculation section 34 calculates the magnitude V of the moving speed of the grip 13b in accordance with the following formula.

$$V_{sj} = \sqrt{v_x^2 + v_y^2 + v_z^2}$$

The grip position calculation section 35 is connected to the grip speed calculation section 34. The grip position calculation section 35 calculates the position of the grip 13b based on the output of the grip speed calculation section 34. When calculating the position, the grip position calculation section 35 performs an integral treatment on the speed having been calculated by the grip speed calculation section 34 in accordance with the following formula at the predetermined sampling intervals dt.

$$P_{sj}(t) = \sum_{n=1}^{t} V_{sj}(n) \cdot dt \ (t = 1, \ldots, N)$$

The second detection section 32 is provided with a head acceleration calculation section 36, a head speed calculation section 37, and a head position calculation section 38. The head acceleration calculation section 36 is connected to the inertial sensor 12. The head acceleration calculation section 36 calculates the acceleration of the club head 13c based on the output of the inertial sensor 12 in accordance with the following formula. In such a calculation of the acceleration as described above, the head acceleration calculation section 36 identifies the position $1_{sh}$ of the club head 13c in accordance with the local coordinate system $\Sigma_s$ unique to the inertial sensor 12. When identifying the acceleration, the head acceleration calculation section 36 obtains the position information from the storage device 16. The storage device 16 stores the position $1_{sh}$ of the club head 13c in advance. The position $1_{sh}$ of the club head 13c can be designated via, for example, the input device 21.

$$a_{sh} = a_s + \dot{\omega}_s \times l_{sh} + \omega_s \times (\omega_s \times l_{sh}) + g$$

The head speed calculation section 37 is connected to the head acceleration calculation section 36. The head speed calculation section 37 calculates the moving speed of the club head 13c based on the output of the head acceleration calculation section 36. When calculating the moving speed, the head speed calculation section 37 performs an integral treatment on the acceleration having been calculated by the head acceleration calculation section 36 in accordance with the following formula at the predetermined sampling intervals dt.

$$V_{sh}(0) = 0$$

$$V_{sh}(t) = \sum_{n=1}^{t} \alpha_{sh}(n) \cdot dt \ (t = 1, \ldots, N)$$

The head position calculation section 38 is connected to the head speed calculation section 37. The head position calculation section 38 calculates the position of the club head 13c based on the output of the head speed calculation section 37. When calculating the position, the head position calculation section 38 performs an integral treatment on the speed having been calculated by the head speed calculation section 37 in accordance with the following formula at the predetermined sampling intervals dt.

$$P_{sh}(t) = \sum_{n=1}^{t} V_{sh}(n) \cdot dt \ (t = 1, \ldots, N)$$

The arithmetic processing circuit 14 is provided with a calculation section 41. The calculation section 41 is connected to the grip speed calculation section 34 of the first detection section 31. The calculation section 41 calculates a variation in the amount of inertia at two different time points during the swing action including the impact based on the amount of inertia detected by the first detection section 31.

The calculation section 41 is provided with a maximum value extraction section 42. The maximum value extraction section 42 is connected to the grip speed calculation section 34. The maximum value extraction section 42 identifies the maximum value of the moving speed of the grip 13b based on the output of the grip speed calculation section 34. The maximum value extraction section 42 identifies a moment (timing) of an appearance of the maximum value during the swing action. In such a manner as described above, the amount of inertia detected at a time point during the swing action is extracted in the maximum value extraction section 42.

The calculation section 41 is provided with an impact point extraction section 43. The impact point extraction section 43 is connected to the grip speed calculation section 34. The impact point extraction section 43 identifies the moving speed of the grip 13b at impact based on the output of the grip speed calculation section 34. The impact point extraction section 43 identifies the moment (timing) of the impact during the swing action. In such a manner as described above, the amount of inertia detected at a time point during the swing action is extracted in the impact point extraction section 43. The time point of the impact is different from the time point of the appearance of the maximum value.

The calculation section 41 is provided with a change rate calculation section 44. The change rate calculation section 44 is connected to the maximum value extraction section 42 and the impact point extraction section 43. The change rate calculation section 44 calculates the change rate $\eta$ of the speed based on the magnitude of the moving velocities extracted by the maximum value extraction section 42 and the impact point extraction section 43.

$$\eta = 1 - \frac{\text{velocity at impact}}{\text{maximum value of velocity}}$$

The arithmetic processing circuit 14 is provided with a graph image data generation section 45. The graph image data generation section 45 is connected to the grip speed calculation section 34 of the first detection section 31 and the head speed calculation section 37 of the second detection section 32. The graph image data generation section 45 generates image data visually expressing the change in the moving speed of the grip 13b and the change in the moving speed of the club head 13c based on the moving speed of the grip 13b and the moving speed of the club head 13c calculated by the grip speed calculation section 34 and the head speed calculation section 37. In the image data, there is drawn a graph visually showing the change in the moving speed in accordance with the time axis.

The arithmetic processing circuit 14 is provided with a swing image data generation section 46. The swing image data generation section 46 is connected to the grip position calculation section 35 of the first detection section 31 and the head position calculation section 38 of the second detection section 32. The swing image data generation section 46 identifies a trajectory of the golf club 13 based on the position of the grip 13b and the position of the club head 13c calculated by the grip position calculation section 35 and the head position calculation section 38. An image expressing the swing action is generated based on the trajectory thus identified. The image is output from the swing image data generation section 46 as the image data.

The arithmetic processing circuit 14 is provided with a superimposed image data generation section 47. The superimposed image data generation section 47 is connected to the maximum value extraction section 42, the impact point extraction section 43, and the swing image data generation section 46. The superimposed image data generation section 47 generates the image data for displaying the moment of the appearance of the maximum value and the moment of the impact in the image expressing the swing action based on the outputs of the maximum value extraction section 42, the impact point extraction section 43, and the swing image data generation section 46.

The arithmetic processing circuit 14 is provided with a drawing section 48 as a display section. The drawing section 48 is connected to the change rate calculation section 44, the superimposed image data generation section 47, the graph image data generation section 45, and the swing image data generation section 46. The drawing section 48 draws an image numerically expressing the change rate based on the output of the change rate calculation section 44. Similarly, the drawing section 48 draws the image for displaying the moment of the appearance of the maximum value and the moment of the impact in the image expressing the swing action based on the output of the superimposed image data generation section 47. The drawing section 48 draws the image visually expressing the change in the moving speed of the grip 13b and the change in the moving speed of the club head 13c based on the output of the graph image data generation section 45, and draws the image expressing the swing action based on the output of the swing image data generation section 46.

(4) Operation of Golf Swing Analysis Device

The operation of the golf swing analysis device 11 will briefly be explained. Firstly, the golf swing of a golfer is measured. Prior to the measurement, the necessary information is input from the input device 21 to the arithmetic processing circuit 14. Here, input of the position $l_{sj}$ of the pivot point 28 in accordance with the local coordinate system $\Sigma_s$, and a rotation matrix $R^0$ of the initial posture of the inertial sensor 12 is prompted. The information thus input is managed under, for example, specific identifiers. It is sufficient for the identifiers to identify specific golfers.

Prior to the measurement, the inertial sensor 12 is attached to the shaft 13a of the golf club 13. The inertial sensor 12 is fixed to the golf club 13 so as to be unable to be displaced relatively to the golf club 13. Here, one of the detection axes of the inertial sensor 12 is adjusted to the axis of the shaft 13a. One of the detection axes of the inertial sensor 12 is adjusted to the target direction identified by the orientation of the face.

Prior to the execution of the golf swing, the measurement by the inertial sensor 12 is started. At the beginning of the action, the inertial sensor 12 is set to a predetermined position and a predetermined posture. The position and the posture correspond to those identified by the rotation matrix $R^0$ of the initial posture. The inertial sensor 12 continuously measures the acceleration and the angular velocity at predetermined sampling intervals. The sampling intervals define the resolution of the measurement. The detection signal of the inertial sensor 12 is fed to the arithmetic processing circuit 14 at real time. The arithmetic processing circuit 14 receives the signal for identifying the output of the inertial sensor 12.

Figure 4:
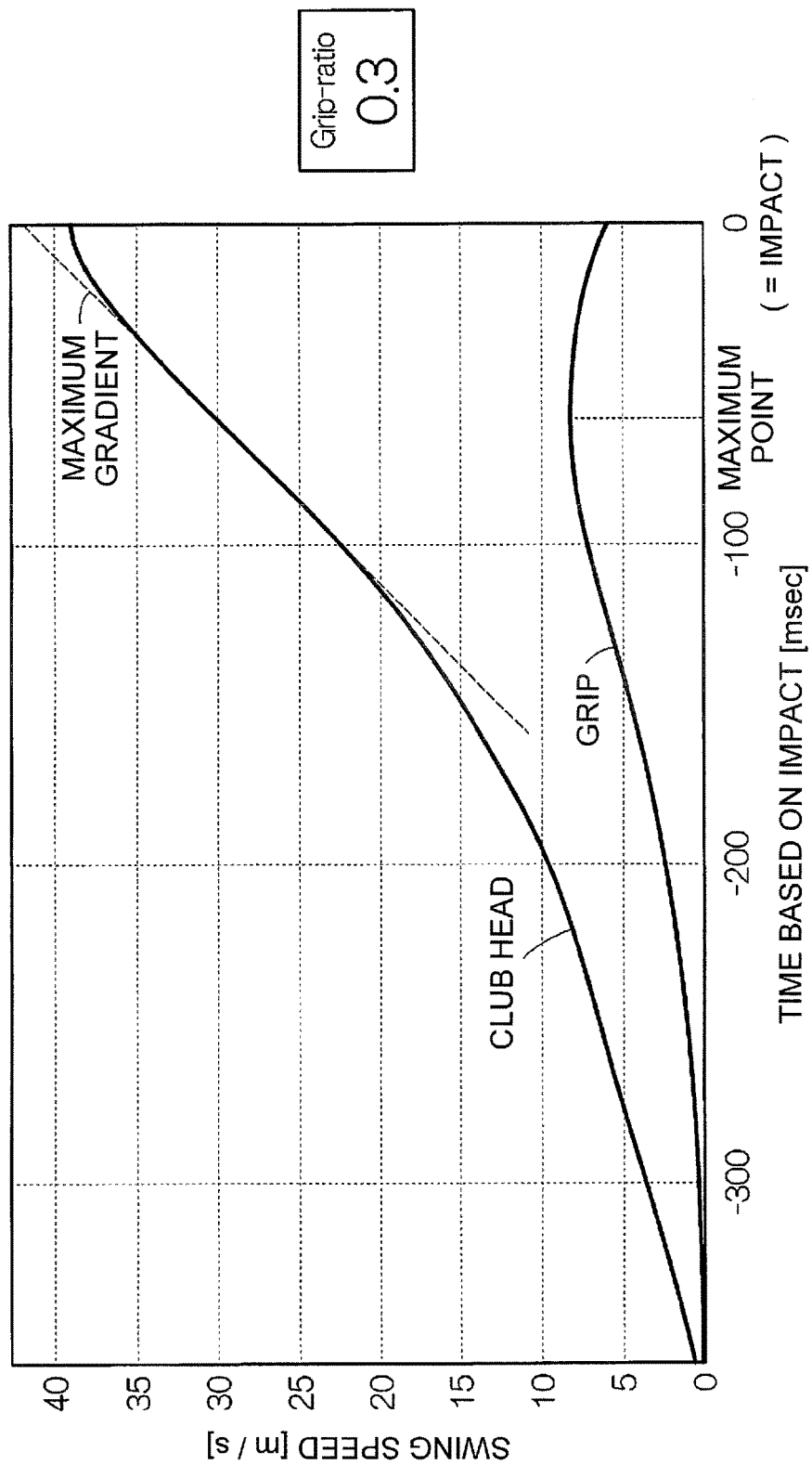
FIG. 4 is a diagram showing a specific example of an image numerically expressing a rate of change, and an image visually expressing a change in moving speed.

A golf swing starts with address, and then reaches follow-through and then finish via swinging up in a backswing, a downswing after a lag, and an impact. The golf club 13 is swung. When the golf club 13 is swung, the posture of the golf club 13 varies in accordance with the time axis. The inertial sensor 12 outputs the detection signal in accordance with the posture of the golf club 13. On this occasion, the grip speed calculation section 34 and the head speed calculation section 37 detect the moving speed of the grip 13b and the moving speed of the club head 13c during the swing action. The maximum value extraction section 42 extracts the maximum value of the moving speed of the grip 13b. The impact point extraction section 43 extracts the moving speed of the grip 13b at impact. The change rate calculation section 44 calculates the change rate of the speed. The ratio between the maximum value of the moving speed and the moving speed at impact is calculated. The drawing section 48 draws the image numerically expressing the change rate. The drawing data is transmitted to the image processing circuit 18. As shown in FIG. 4, the change rate "0.3" of the speed is displayed on the screen. The deceleration of the grip 13b is identified based on the change rate of the speed. The deceleration of the grip 13b having been identified in such a manner as described above is presented to the subject. The magnitude of the change rate reflects how the force is decreased immediately before the impact. Therefore, the subject can check how the force is decreased immediately before the impact based on the change rate of the speed. The subject can improve the form of the swing in accordance with how the force is decreased thus checked.

In accordance with the time axis, the motion of the grip 13b is decelerated from the maximum value of the moving speed. Therefore, if the maximum value of the moving speed is identified, the deceleration of the moving speed is surely identified. If the deceleration does not occur in the moving speed of the grip 13b, the moving speed at impact directly corresponds to the maximum value of the moving speed. As a result, the change rate shows "0 (zero)." In such a manner as described above, the subject can confirm that the deceleration of the grip 13b fails to be established before the impact.

The graph image data generation section 45 generates the image data visually expressing the change in the moving speed of the grip 13b and the change in the moving speed of the club head 13c. The drawing section 48 draws the image visually expressing the change in the moving speed of the grip 13b and the change in the moving speed of the club head 13c. The drawing data is transmitted to the image processing circuit 18. As shown in FIG. 4, the graph is drawn on the screen. In such a manner as described above, the change in the moving speed of the grip 13b and the change in the moving speed of the club head 13c are visually presented to the subject. The subject can check increase in the head speed caused in accordance with the deceleration of the grip 13b. The subject can recognize the importance of the deceleration of the grip 13b. The subject can improve the form of the swing in accordance with the change in the moving speed thus presented. Specifically, by displaying the moving speed of the club head 13c and the moving speed of the grip 13b attached with the inertial sensor 12 on the same screen of the display section, the subject can check the timing of weakening the force during the swing, and the increase in moving speed of the club head 13c after that timing.

It should be noted that although the example of the moving speed is explained as the amount of inertia, it is also possible to calculate the maximum value and the change using the amount of inertia such as the acceleration output from the acceleration sensor or the angular velocity output from the angular velocity sensor, and then present them to the subject besides the example. Further, besides the presentation of the maximum value of the amount of inertia, it is also possible to calculate the change in the amount of inertia at at least two different time points, and then use the change as an indicator for timing the deceleration of the grip 13b.

Figure 5:
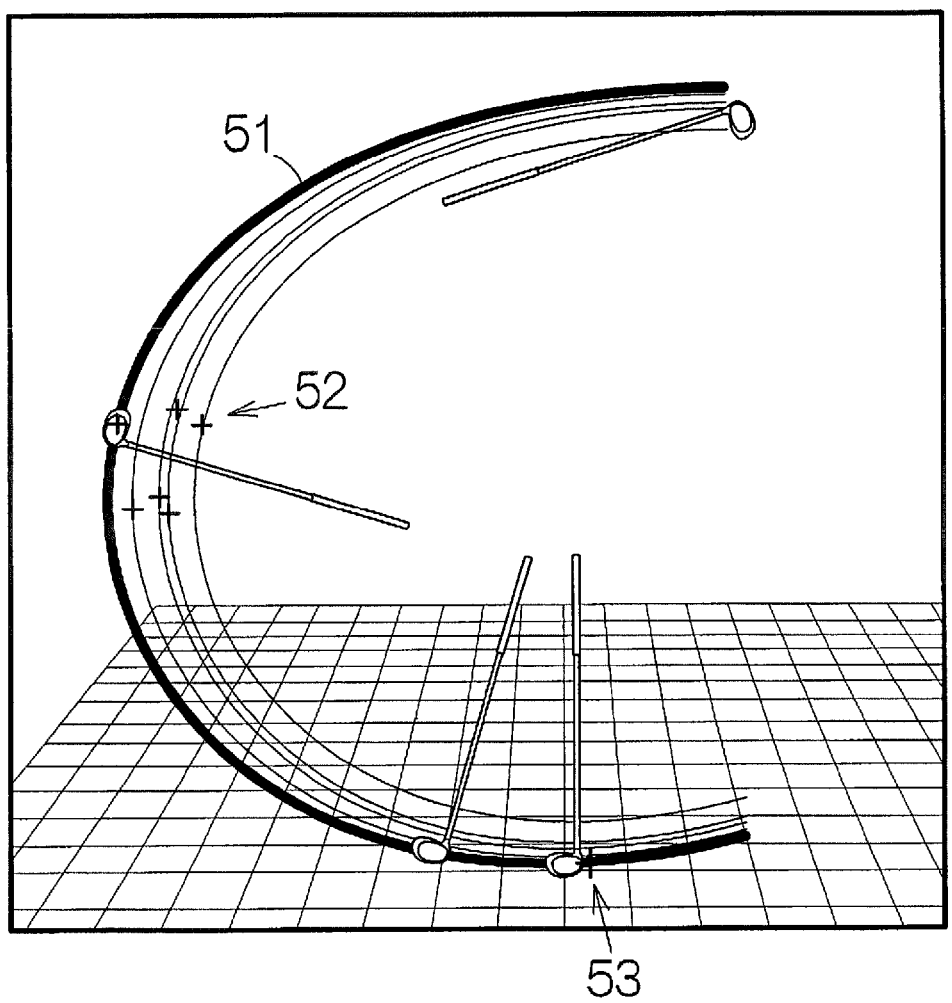
FIG. 5 is a diagram showing a specific example of an image for displaying a moment when the maximum value appears and a moment of the impact in addition to the image expressing the swing action.

The swing image data generation section 46 identifies the trajectory of the golf club 13. An image expressing the swing action is generated based on the trajectory thus identified. The image is transmitted to the drawing section 48 as the image data. The drawing section 48 draws the image expressing the swing action. The drawing data is transmitted to the image processing circuit 18. As a result, as shown in, for example, FIG. 5, the motion trajectory 51 of the golf club 13 is reproduced on the screen. The swing action is expressed by the motion trajectory 51. Here, the superimposed image data generation section 47 generates the image data for displaying the moment 52 of the appearance of the maximum value and the moment 53 of the impact in the image expressing the swing action. The drawing section 48 draws the image for displaying the moment 52 of the appearance of the maximum value and the moment 53 of the impact in the motion trajectory 51. The drawing data is transmitted to the image processing circuit 18. As a result, as shown in FIG. 5, the two different time points 52, 53, namely the moment of the appearance of the maximum value and the moment of the impact, are displayed in the image of the motion trajectory of the swing action. In such a manner as described above, the deceleration of the grip 13b is visually presented to the subject. The subject can clearly figure out the position of the deceleration of the grip 13b during the swing action. The subject can improve the form of the swing in accordance with the moment of the deceleration of the grip 13b presented in such a manner.

As described above, in the golf swing analysis device 11, the three-dimensional motion analysis model 26 can be used when analyzing the motion. In the three-dimensional motion analysis model 26, the golf club 13 is applied to the rod 27. The grip 13b corresponds to the pivot point 28 three-dimensionally supported in the space. According to the three-dimensional motion analysis model 26, the moving speed of the grip 13b is calculated only by mounting the single inertial sensor 12 on the golf club 13. It should be noted that it is also possible for the inertial sensor 12 to be mounted on, for example, a hand or an arm of the subject instead of the golf club 13, and even in such a case, the acceleration, the speed, and the displacement of the grip 13b and the club head 13c are derived by single inertial sensor 12.

It should be noted that in the embodiment described hereinabove, each of the functional blocks of the arithmetic processing circuit 14 is realized in accordance with the execution of the golf swing analysis software program 17. It should also be noted that each of the functional blocks can also be realized by the hardware without resort to the software processing. Besides the above, the golf swing analysis device 11 can also be applied to the swing analysis of sporting equipment (e.g., a tennis racket, a table-tennis racket, a baseball bat, and a bamboo sword called shinai in kendo) held by hand and then swung.

Although the present embodiment is hereinabove explained in detail, it should easily be understood by those skilled in the art that it is possible to make a variety of modifications not substantially departing from the novel matters and the advantages of the invention. Therefore, such modified examples are all included in the scope of the invention. For example, a term described at least once with a different term having a broader sense or the same meaning in the specification or the accompanying drawings can be replaced with the different term in any part of the specification or the accompanying drawings. Further, the configurations and the operations of the golf club 13, the grip 13*b*, the club head 13*c*, the arithmetic processing circuit 14, the first detection section 31, the calculation section 41, and so on are not limited to those explained in the embodiment, but can variously be modified. Further, the invention can also be applied to the sports using the swing action such as tennis or baseball beside golf.

The entire disclosure of Japanese Patent Application No. 2013-130654, filed Jun. 21, 2013 is expressly incorporated by reference herein.

What is claimed is:

1. A motion analysis method comprising:
    while a sporting equipment is being used by a user:
        receiving sensor data from an inertial sensor attached to a shaft of the sporting equipment used for swinging, the inertial sensor being attached to the shaft in a grip portion of the shaft;
        detecting, based on the received sensor data, moving speeds of the grip portion and moving speeds of a head of the sporting equipment during a swing action;
        extracting, from among the moving speeds, a maximum value of the moving speeds of the grip portion, and a moving speed of the grip portion at impact;
        calculating a rate of change of the maximum value of the moving speeds of the grip portion and the moving speed of the grip portion at impact;
        identifying a deceleration value of the grip portion based on the calculated rate of change; and
        causing a display to display data regarding the identified deceleration value of the grip portion.

2. The motion analysis method according to claim 1, further comprising:
    calculating a ratio between the maximum value of the moving speeds of the grip portion and the moving speed of the grip portion at the impact.

3. The motion analysis method according to claim 1, comprising:
    calculating a change in an amount of inertia of the grip portion during the swing action; and
    detecting a timing when the amount of inertia turns from increase to decrease during the swing action.

4. The motion analysis method according to claim 3, wherein the amount of inertia is a moving speed.

5. The motion analysis method according to claim 3, wherein
    the timing when the amount of inertia turns from increase to decrease is displayed together with a motion trajectory of the swing.

6. The motion analysis method according to claim 1, further comprising:
    causing the display to display a change in the detected moving speeds of the grip portion during the swing action in a time-series manner.

7. The motion analysis method according to claim 1, further comprising:
    causing the display to display at least one of the detected moving speeds of the grip portion during the swing action and the detected moving speeds of the head of the sporting equipment during the swing action.

8. The motion analysis method according to claim 1, wherein
    the sporting equipment is at least one of: a golf club, a tennis racket, a table-tennis racket, a baseball bat, and a bamboo sword.

9. The motion analysis method according to claim 1, wherein
    the displayed data includes data that visually expresses a change in the moving speed of the grip and a change in the moving speed of the head.

10. The motion analysis method according to claim 1, further comprising:
    fixing a local coordinate system to the inertial sensor, the origin of the local coordinate system being set to the origin of a detection axis of the inertial sensor, the y axis of the local coordinate system coinciding with the center of the shaft, the x axis of the local coordinate system coinciding with a target direction identified by an orientation of a face of the head of the sporting equipment; and
    identifying, in accordance with the local coordinate system, at least one of: a position of a pivot point, a position of a centroid, and a position of the head.

11. The motion analysis method according to claim 10, wherein
    each of the position of the pivot point, the position of the centroid, and the position of the head is identified.

12. A motion analysis device comprising:
    at least one circuit or processor configured to:
    while a sporting equipment is being used by a user:
        receive sensor data from an inertial sensor attached to a shaft of a-the sporting equipment used for swinging, the inertial sensor being attached to the shaft in a grip portion of the shaft;
        detect, based on the received sensor data, moving speeds of the grip portion and moving speeds of a head of the sporting equipment during a swing action;
        extract, from among the moving speeds, a maximum value of the moving speeds of the grip portion, and a moving speed of the grip portion at impact;
        calculate a rate of change of the maximum value of the moving speeds of the grip portion and the moving speed of the grip portion at impact;
        identify a deceleration value of the grip portion based on the calculated rate of change; and
        cause a display to display data regarding the identified deceleration value of the grip portion.

* * * * *